(12) United States Patent
Piepenbrock et al.

(10) Patent No.: US 8,577,615 B2
(45) Date of Patent: Nov. 5, 2013

(54) METHOD FOR QUANTITATIVE DETERMINATION OF THE DEGREE OF METHYLATION OF CYTOSINES IN CPG POSITIONS

(75) Inventors: Christian Piepenbrock, Berlin (DE); Jörn Lewin, Berlin (DE); Armin Schmitt, Berlin (DE)

(73) Assignee: Epigenomics AG, Berlin (DE)

( * ) Notice: Subject to any disclaimer, the term of this patent is extended or adjusted under 35 U.S.C. 154(b) by 1059 days.

(21) Appl. No.: 10/455,212

(22) Filed: Jun. 5, 2003

(65) Prior Publication Data

US 2004/0023279 A1 Feb. 5, 2004

(30) Foreign Application Priority Data

Jun. 5, 2002 (EP) ..................................... 02090203

(51) Int. Cl.
*G06F 19/00* (2011.01)
*C12Q 1/68* (2006.01)

(52) U.S. Cl.
USPC .................................................. 702/19; 435/6

(58) Field of Classification Search
None
See application file for complete search history.

(56) References Cited

U.S. PATENT DOCUMENTS 6,218,121 B1 * 4/2001 Simpson et al. .................. 435/6
6,844,151 B1 * 1/2005 Dale ................................. 435/6

FOREIGN PATENT DOCUMENTS

EP 0535587 * 4/1992
WO WO 98/56952 A1 12/1998

OTHER PUBLICATIONS

Paul et al. Cytosine methylation: Quantitation by automated genomic sequencing and GENESCAN analysis. BioTechniques, vol. 21, pp. 126-133, Jul. 1996.*

Aggerholm et al. Entensive Intra- and Interindividual Heterogeneity of p15INK4B Methylation Acute Myeloid Leukemia. Cancer Research, vol. 59, 1999, pp. 436-441.*
Paquin et al. A spontaneous chormosomal amplification of the ADH2 gene in *Saccharomyces cerevisiae*. Genetics, vol. 130, 1992, pp. 263-271.*
Foley JP. Equations for chromatographic peak modeling and calculation of peak area. Analytical Chemistry, 1987, vol. 59, pp. 1984-1987.*
Rein et al. Active mammalian replication origins are associated with a high-density cluster of mCpG dinucleotides. Molecular and Cellular Biology. 1997, vol. 17, pp. 416-426.*
Larson et al. Calculus with analytic geometry; Alternate fourth edition. Lexington, Massachusetts: D. C. Heath and Company, 1990, inside back cover, one page.*
Definition of "Electropherogram." The American Heritage Medical Dictionary, 2007, one page; retrieved online on Mar. 25, 2010 from << http://www.credoreference.com >>.*
Cronin et al. Cystic fibrosis mutation detection by hybridization to light-generated DNA probe arrays. Human Mutation, 1997, vol. 7, pp. 244-255.*
DNA. The Penguin Dictionary of Science, 2009, one page. Obtained online on Aug. 7, 2011 from <<http://www.credoreference.com/entry/penguinscience/dna>>.*
El-Maarri et al., "A rapid, quantitative, non-radioactive bisulfite-SNuPE-IP RP HPLC assay for methylation analysis at specific CpG sites," Nucleic Acids Research, 30(6)e25:1-4 (2002).

* cited by examiner

*Primary Examiner* — Lori A Clow
(74) *Attorney, Agent, or Firm* — Kriegsman & Kriegsman (57) ABSTRACT

The invention describes a method for the quantitative sequencing of nucleic acids treated with bisulfite. The invention particularly describes a method for the determination of the degree of methylation of a cytosine in the base sequence 5'-CG-3', thus in a so-called CpG position, if the genomic sequence of the investigated DNA region is known. The invention makes possible the validation of sequence information in the sequencing of DNA treated with bisulfite. It is particularly described how the data obtained with conventional sequencing methods are first standardized with respect to their signal intensity, how the conversion rate of cytosine to uracil after bisulfite treatment is determined from these data, and how a correction factor can be determined with the help of this conversion rate, and this factor produces an essentially improved estimation of the degree of methylation actually present.

19 Claims, 2 Drawing Sheets

METHOD FOR QUANTITATIVE DETERMINATION OF THE DEGREE OF METHYLATION OF CYTOSINES IN CPG POSITIONS

The invention concerns a method for the determination of the degree of methylation of a cytosine to be investigated in the genome of at least one cell or at least one organism.

PRIOR ART

5-Methylcytosine is the most frequent covalently modified base in the DNA of eukaryotic cells. For example, it plays a role in the regulation of transcription, in genomic imprinting and in tumorigenesis. The identification of 5-methylcytosine as a component of genetic information is thus of considerable interest. 5-Methylcytosine positions, however, cannot be identified per se by sequencing, since 5-methylcytosine has the same base-pairing behavior as cytosine. In addition, in the case of a PCR amplification, the epigenetic information which is borne by the 5-methylcytosines is completely lost.

Several methods are known which solve these problems. For the most part, a chemical reaction or enzymatic treatment of the genomic DNA is conducted, as a consequence of which, cytosine bases can be distinguished from methylcytosine bases. One familiar method is the conversion of genomic DNA with bisulfite, which leads to a conversion of cytosine bases to uracil in two steps after alkaline hydrolysis (Shapiro, R., Cohen, B. and Servis, R. (1970) Nature 227, 1047). 5-Methylcytosine remains unchanged under these conditions. The conversion of cytosine to uracil leads to a change of the base sequence, from which the original 5-methylcytosines can now be determined by sequencing (only these bases appear as a band in the C lane).

An overview of other known possibilities for detecting 5-methylcytosines can be derived from the following review article along with the literature cited therein: Rein, T., DePamphilis, M. L., and Zorbas, H., (1998) Nucleic Acids Res. 26, 2255.

The determination of a base sequence based on the addition of suitable oligonucleotides which bind to DNA and function as primer molecules, which are then extended by means of a DNA polymerase and sufficient dNTPs as well as ddNTPs leading to a break in the chain, is also state of the art. This method is named in the following as the chain termination or the Sanger sequencing method. The most modern sequencing methods, which permit an automation of sequencing, are based on a combination of this concept with the polymerase chain reaction (PCR) and computer-supported evaluation programs.

The amplification of DNA by means of PCR is state of the art. Automated sequence analysis is also state of the art. Essentially, the Sanger sequencing method is used for the automation, in which four reactions are distinguishable in terms of which one of the four bases is added in each as ddNTP to the reaction mixture, also comprising the DNA template and the four dNTPs. This then leads to the termination of the polymerase reaction at this base in each of said reactions. If four reaction batches are prepared and oligonucleotide primers that are specifically fluorescently labeled are used for each batch, then even after mixing the terminated reaction batches, the batch from which a molecule originates can still be determined with suitable detectors. It is thus possible to separate this mixture according to size in one lane.

In order to circumvent the relatively time-consuming and expensive fluorescent labeling of the oligonucleotide primers, the termination dideoxy nucleotides can also be fluorescently labeled with different dyes. In this case, the separation into four reaction batches is not necessary and all four termination reactions can occur concurrently.

After the reaction has terminated, the fluorescently labeled reaction products are separated according to their size in one lane of an acrylamide gel by electrophoresis. The DNA fragments migrating past the detector sequentially according to size are irradiated by a laser, which excites the fluorescent dye and induces the emission of its specific wavelength. These are recorded by the detector and translated to sequence information with suitable computer programs.

The automated methods that are currently used supply an electropherogram as a result of this compilation of emission data, i.e., a graphic representation of the data, for each of the four dyes. Since each dye is associated with a specific nucleic acid, the base sequence in the original sequence can thereby be determined.

Several articles are named below which concern the prior art of "bisulfite sequencing", i.e., the sequence analysis of bisulfite-treated DNA:

For example, the technique of bisulfite sequencing has been used both for the methylation analysis of the minimal promoter of the androgen receptor (Kinoshita et al., Methylation of the Androgen Receptor Minimal Promoter Silences Transcription in Human Prostate Cancer (2000) Cancer Research 60, 3623-3630), as well as for the methylation analysis of the glutathione-S-transferase-π-gene (Millar et al. (1999); Detailed methylation analysis of the glutathione-S-transferase π (GSTP1) gene in prostate cancer. Oncogene 18, 1313-1324) for clarification of its role in prostate cancer. In both articles, the authors refer to an article by Susan J. Clark et al. (High sensitivity mapping of methylated cytosines. (1994) Clark et al.; Nucleic Acids Res 22, 2990-2997), in which the method of bisulfite sequencing is described.

The prior art relative to the quantitative determination of cytosine methylation by means of sequencing methods can be taken principally from an article of Paul and Clark, in which a method of sequencing is described with the use of differently labeled thymine and cytosine bases (Paul C. L. and Clark S. J. (1996) Cytosine methylation: quantitation by automated genomic sequencing and GENESCAN analysis. Biotechniques. 21(1), 126-33). The method in principle is suitable for conducting quantitative analysis of the degree of methylation. It does not solve the problem, however, that due to the different rates of incorporation of thymine and cytosine, as well as due to the use of different dyes, a precise quantification is very difficult. This problem is solved by the standardization proposed in the invention described herein. In addition, the method described by Clark and Paul in no way considers the efficiency of the conversion reaction, which converts the unmethylated cytosine into bases with the hybridization behavior of thymines, and thus considerably influences the result. The consideration of the bisulfite conversion rate, however, is an essential step of the method of the present invention.

DESCRIPTION OF THE PROBLEM AND ITS SOLUTION

In an electropherogram, as mentioned above, the sequence of bases in the sequence is represented as a curve plot. Theoretically, each peak of this curve plot corresponds to the appearance of a base in the original sequence. Thus, graphs of four different colors are superimposed in order to determine the entire sequence.

Since each position can only be occupied once in an individual sequence, and likewise each position must be represented by at least one base, in the ideal case, all signals must have the same intensity. The signal intensity is determined by the size of the peak, or stated more precisely, by the area under the peak. These areas should be of equal size, as long as the incorporation of the termination nucleotides is distributed randomly and is uniform. In contrast, for the favored incorporation of a termination nucleotide at one position, this product is present in increased quantity and the corresponding peak is larger. The base sequence, however, remains unaffected by this.

Also, the different intensity of the fluorescent dyes used causes different signal intensities. This does not play a role in the qualitative determination of the sequence itself, however, if one is investigating a mixture of sequences which differ in their base sequence at individual positions, and if one wants to determine the ratio of those specific sequences, the correct determination of the peak intensity becomes extremely important. The intensity of a peak reflects the number of molecules in the DNA mixture, which have these specific bases at those positions. If, for example, two alleles have different nucleotides at one position, one obtains two peaks of half intensity over one another, so to speak, at the same position in the electropherogram. This is the case, for example, when point mutations which appear only on one allele, are analyzed.

The determination of the peak intensity is consequently always of decisive importance, if the fraction of a specific base sequence is to be quantified from a mixture of similar sequences. This is the case, if one wants to determine the degree of methylation of one or more cytosines. The quantitative determination of the degree of methylation of a cytosine is to be understood as the determination of the fraction of methylated DNA molecules in a mixture of methylated and unmethylated DNA molecules.

Methylated cytosines can be distinguished from unmethylated cytosines by means of a suitable conversion, for example, bisulfite treatment. The converted sequences can be analysed on the basis of their different hybridization behavior e.g. by means of PCR. Consequently, after PCR a mixture of molecules is present, which are distinguishable from one another at individual nucleotides. If, for example, 20% of the molecules are methylated at a CpG position, when sequencing the bisulfite-treated DNA a peak with a signal intensity of 20% should appear at that position in the cytosine-detecting electropherogram, while in the thymine-detecting electropherogram, a peak with a signal intensity of 80% of the otherwise normal signal intensity should appear. In order to be able to utilise the peak intensities for an accurate quantification, it must, of course, be assumed that the signal intensities obtained are identical for all four colors. This, however, is not the case.

Conversely, it can in no way be assumed that all four fluorescent dyes are detected with equal intensity, nor that all four rates of incorporation are effectively the same. Particularly in the sequencing of DNA treated with bisulfite, the problem arises that there are relatively very few cytosines in the modified sequence and these signals thus appear essentially more intense. Based on this extreme imbalance of the sequence fragments labeled with different colors, an overestimation of the signal intensity of the cytosine label occurs and thus the result of the sequence analysis is misleading.

In order to obtain more reliable sequence information, particularly if one would like to obtain not only a yes/no qualitative answer, but would like to determine quantitatively the fraction of a base at a specific position of the sequence, a standardization of the different signals relative to one another is recommended. On the other hand, if this involves the determination of the fraction of cytosines in a bisulfite-treated cytosine-poor sequence, the standardization is absolutely necessary, particularly of the cytosine signal.

Another essential problem results from the fact that the conversion of unmethylated cytosine to uracil often is incomplete. For example, a conversion rate of 80% has the consequence that 20% of the (unmethylated) cytosines, which should actually give a thymine signal after the conversion to uracil and after PCR, do not do so. Therefore, at CpG positions where the cytosine is 100% unmethylated, the signal intensity of thymine at the position of unmethylated cytosines is only 80% in comparison to the average guanine signal intensity. Without knowing the conversion rate and assuming that the transformation has been complete, this signal intensity would be interpreted as 80% unmethylated and 20% methylated cytosines at the CpG position. Therefore, the determination of the conversion rate is absolutely necessary as the standardization of intensities for the accurate quantification of the degree of methylation of a cytosine.

Most of the state of the art which is concerned with "gene silencing", the down-regulation of gene transcription and methylation, is based on qualitative methylation analyses, which are limited to the analysis of one or a few CpG positions by means of methylation sensitive restriction enzymes. More in-depth analyses, which investigate, for example, the degree of methylation at different alleles, are based on sequencing of clones (Kinoshita et al., 2000; Cancer Research 60, 3623-3630): The genomic DNA to be investigated is extracted and treated with bisulfite. The DNA regions of interest are amplified by means of PCR and the obtained amplificates are subcloned.

If the methylation state of specific alleles is to be determined, the PCR amplificates of the DNA treated with bisulfite are subcloned and for example, transformed in *E. coli*. Subsequently, 10-25 individual colonies of each clone are investigated. In the methylation analysis of an allele, in which the result can only be zero, one or two, even a relatively small number of colonies can provide a large amount of informationright after sequencing. Generally, however, the more colonies are investigated, the closer the result will correspond to the actually present degree of methylation. In the cited document (Kinoshita et al. 2000 ) 10-25 *E. coli* cultures are grown and the plasmid DNA is isolated from each of these. These 10-25 plasmid DNA samples are all sequenced individually and the degree of methylation of the allele is determined on the basis of the ratio of methylated and unmethylated clones.

The multiple sequencing of the DNA and particularly also the additional step of cloning makes this process costly in terms of material and labor.

In the above-given studies (Kinoshita et al., 2000 and Millar et al., 1999), attempts for quantitatively determining the degree of methylation of a CpG position without the need for cloning are also described. The interpretation of the data, however, in both cases, is done without having determined the efficiency of the bisulfite reaction, and thus without having considered it for the calculation of the actual degree of methylation. The distortion of the signal intensities is also not be taken into consideration. The described conventional methods for determining DNA methylation at CpG positions by means of sequencing are thus not only expensive and tedious, but also produce potentially false results, particularly in the case of more complex sample mixtures.

SUMMARY OF THE INVENTION

The described problems and disadvantages of the prior art are solved by the method according to the invention.

The object is thus solved according to the invention by a method for the determination of the degree of methylation of a cytosine to be investigated in the genome of at least one cell or one organism, in which the following steps are conducted:
a) Treatment of a DNA sample with bisulfite and subsequent amplification of a selected fragment of this treated DNA;
b) Conducting a sequence analysis of the amplificate, in which the result is represented in the form of an electropherogram;
c) Determination of a conversion rate of cytosine to uracil as a consequence of bisulfite treatment, characterized in that the ratio of the signal intensity of bases which modify their hybridization behavior due to bisulfite treatment to the signal intensity of bases which do not modify their hybridization behavior due to bisulfite treatment is determined, wherein one optionally uses the sense sequence and/or its inversely complementary sequence;
d) Calculation of the actual degree of methylation of the cytosine to be investigated taking into consideration the conversion rate determined in step c).

Thus, it is preferred according to the invention that one determines only the thymine sequence, or in the inversely-complementary strand, only the adenine sequence of the DNA and represents the result in the form of an electropherogram.

According to the invention, the signal intensity $I_B$ of a base B, wherein B can be either C, A, G or T, and thus determines the type of base whose intensity is represented, is described as a part of the area under the peak in the electropherogram by the following formula, wherein f(x) describes the curve of the intensity signal over a unit x, which represents time, which describes the distance between two bases after chromatographic separation:

$$I_B = \int_{W1}^{W2} f(x)\,dx$$

wherein W1 and W2 are the x-coordinates of the points of inflection closest to the x value of the maximum $f_{max}$ and W1 lies to the left and W2 to the right of this x value.

According to the invention, however, the signal intensity $I_B$ is also described by the following formula:

$$I_B = \int_{M1}^{M2} f(x)\,dx$$

wherein M1 and M2 are the x-coordinates of the minima closest to the x value of the maximum $f_{max}$ and M1 lies to the left and M2 to the right of this x value.

According to the invention, however, the signal intensity $I_B$ is also described by the following formula:

$$I_B = \int_{H1}^{H2} f(x)\,dx$$

wherein H1 and H2 are the x-coordinates of the positions in the curve at which f(x) is one-half $f_{max}$, closest to the x value of the maximum $f_{max}$, and H1 lies to the left and H2 to the right of this x value.

Finally, according to the invention, the signal intensity $I_B$ is also described by the following formula:

$$I_B = \int_{D1}^{D2} f(x)\,dx$$

wherein $$D1 = x - (x - x\_left)/2 \text{ and}$$

$$D2 = x + (x\_right - x)/2,$$

wherein
x is the x-coordinate of the position A of the signal intensity to be determined
x_left is the x-coordinate of the maximum of the peak to the left thereof and
x_right is the x-coordinate of the maximum of the peak to the right thereof.

Finally, according to the invention, the signal intensity $I_B$ of a signal at a position A can be calculated as the area under the signal curve according to the following formula:

$$I_B = \int_{X1}^{X2} f(x)\,dx$$

wherein the x-coordinates of a random combination of the values, W1, W2, H1, H2, M1, M2, D1 or D2 as described above can be used as limiting values X1 and X2, but X1 must lie to the left and X2 to the right of the x-value that determines position A.

According to the invention, a method is also included in which the sequence analysis is conducted according to the chain termination method.

According to the invention, it is also particularly preferred that a sequence analysis for at least two different bases is conducted in step b), and wherein another step follows, in which a standardizing of the average signal intensity of at least one base type (C, T, A or G) against the average signal intensity which is obtained for one or more of the remaining base types is performed, wherein the average of a plurality of positions of this base type is determined within an arbitrarily defined region of the amplificate. A plurality of positions in connection with this invention is to be understood as at least two positions. However, it may also be more than two, up to a number of up to 100 positions and more. It is extremely important that averaging leads to mathematically reasonable and/or statistically reliable values.

It is further preferred that previously standardized signal intensities are used for the determination of the named conversion rates in step c).

It is further particularly preferred that both the standardized signal intensities as well as the conversion rates obtained taking into consideration the standardized signal intensities are used for the calculation of the actual degree of methylation of the cytosine to be investigated.

According to the invention, it is thus most particularly preferred that the signal intensity of the cytosine signals is standardized against the signal intensity of the thymine signals or, when utilizing the sequence information of the inversely complementary strand, the signal intensity of the guanine signals is standardized against the signal intensity of the adenine signals.

According to the invention, the factor for standardization $f_N$ is calculated from $$f_N = <I_C^{CG}>/(<I_T^T> - <I_T^{CG}>)$$

or from its reciprocal value $$f_N^{-1} = (<I_T^T> - <I_T^{CG}>)/<I_C^{CG}>$$

or, respectively, when utilizing the sequence information of the inversely complementary strand, $$f_N = <I_G^{CG}>/(<I_A^A> - <I_A^{CG}>)$$

or from its reciprocal value $$f_N^{-1} = <I_A^A> - <I_A^{CG}>)/<I_G^{CG}>$$

wherein $<I_T^T>$ represents the average thymine signal intensity ($I_T$) and $<I_A^A>$ represents the average adenine signal intensity ($I_A$) at positions, which were also thymine or adenine prior to bisulfite treatment; wherein $<I_T^{CG}>$ and $<I_C^{CG}>$ represent the average thymine and cytosine signal intensities at cytosines in CpG positions; and wherein $<I_A^{CG}>$ and $<I_G^{CG}>$, respectively, represent the average adenine and guanine signal intensities at guanines in CpG positions; and wherein the average of all of the considered positions is taken each time within a randomly defined sequence region.

According to the invention, the factor for standardization $f_N$, however, is also calculated from $$f_N = <I_C^C>/(<I_T^T> - <I_T^C>)$$

or from its reciprocal value $$f_N^{-1} = (<I_T^T> - <I_T^C>)/<I_C^C>$$

or, respectively, when utilizing the sequence information of the inversely complementary strand, $$f_N = <I_G^G>/(<I_A^A> - <I_A^G>)$$

or from its reciprocal value $$f_N^{-1} = (<I_A^A> - <I_A^G>)/<I_G^G>$$

wherein $<I_T^T>$ represents the average thymine signal intensity ($I_T$) and $<I_A^A>$ represents the average adenine signal intensity ($I_A$) at positions, which were also thymine or adenine prior to bisulfite treatment;
wherein $<I_T^C>$ and $<I_C^C>$ represent the average thymine and cytosine signal intensities at cytosines and $<I_A^G>$ and $<I_G^G>$ represent the average adenine and guanine signal intensities at guanines, which do not stand in CpG positions, and wherein the average of all of the considered positions is taken each time within a randomly defined sequence region.

In addition, according to the invention, the factor for standardization $f_N$ is also calculated from $$f_N = <I_T^{A,G}>/<I_C^{A,G}>$$

or from its reciprocal value $$f_N^{-1} = <I_C^{A,G}>/<I_T^{A,G}>$$

or, respectively, when utilizing the sequence information of the inversely complementary strand, $$f_N = <I_A^{T,C}>/<I_G^{T,C}>$$

or from its reciprocal value $$f_N^{-1} = <I_G^{T,C}>/<I_A^{T,C}>$$

wherein $<I_T^{A,G}>$ represents the average thymine signal intensity ($I_T$) and $<I_C^{A,G}>$ the average cytosine signal intensity ($I_C$) at adenine or guanine positions; and wherein $<I_A^{T,C}>$, respectively, represents the average adenine signal intensity ($I_A$) and $<I_G^{T,C}>$ represents the average guanine signal intensity ($I_G$) at thymine or cytosine positions; and wherein the average of all of the considered positions is taken each time within a randomly defined sequence region.

According to the invention, the conversion rate fCoN is calculated from $$f_{CON} = I_T^C/(f_N I_C^C + I_T^C)$$

or $$f_{CON} = <I_T^C/(f_N I_C^C + I_T^C)>$$

or from its reciprocal value $$f_{CON}^{-1} = (f_N I_C^C + I_T^C)/I_T^C$$

or $$f_{CON}^{-1} = <(f_N I_C^C + I_T^C)/I_T^C>$$

or, respectively, when utilizing the sequence information of the inversely complementary strand, $$f_{CON} = I_A^G/(f_N I_G^G + I_A^G)$$

or $$f_{CON} = <I_A^G/(f_N I_G^G + I_A^G)>$$

or from its reciprocal value $$f_{CON}^{-1} = (f_N I_G^G + I_A^G)/I_A^G$$

or $$f_{CON}^{-1} = <(f_N I_G^G + I_A^G)/I_A^G>$$

wherein, each time depending on which standardization is applied, $f_N$ is one of the above-defined standardization factors;
wherein $I_T^C$ represents the thymine signal intensity and $I_C^C$ the cytosine signal intensity of a cytosine not found in a CpG position, and, respectively, $I_A^G$ represents the adenine signal intensity and IGG represents the guanine signal intensity of a guanine not found in a CpG position, after bisulfite treatment;
and wherein either the average of the corresponding quotients of all considered positions within a randomly defined sequence region is taken or only one cytosine or guanine position is considered.

According to the invention, the conversion rate $f_{CON}$, however, is also calculated from $$f_{CON} = <I_T^C>/<I_T^T>$$

or from its reciprocal value $$f_{CON-1} = <I_T^T>/<I_T^C>$$

or, respectively, when utilizing the sequence information of the inversely complementary strand, $$f_{CON} = <I_A^G>/<I_A^A>$$

or from its reciprocal value $$f_{CON}^{-1} = <I_A^A>/<I_A^G>$$

wherein $<I_T^C>$ represents the average thymine signal intensity of a cytosine not found in a CpG position and $<I_A^G>$ represents the average adenine signal intensity of a guanine not found in a CpG position, after bisulfite treatment and $<I_T^T>$ represents the average thymine signal intensity at a thymine position and $<I_A^A>$ represents the average adenine signal intensity at an adenine position, and wherein all of the considered positions are averaged within a randomly defined sequence region.

According to the invention, the methylation number $f_{MET}$ is calculated according to the following formula $$f_{MET} = 1 - I_T^{CG}/(f_{CON}(f_N I_C^{CG} + I_T^{CG}))$$

or, respectively, when utilizing the sequence information of the inversely complementary strand, $$f_{MET}=1-I_A^{CG}/(f_{CON}(f_N I_G^{CG}+I_A^{CG}))$$

wherein $I_T^{CG}$ and $I_C^{CG}$ represent the thymine and cytosine signal intensities of the investigated cytosine in CpG position and $I_A^{CG}$ and $I_G^{CG}$, respectively, represent the adenine and guanine signal intensities of the investigated guanine in CpG position; and wherein a methylation number of 1 corresponds to a 100% methylation.

According to the invention, the methylation number $f_{MET}$ is also calculated according to the following formula $$f_{MET}=1-I_T^{CG}/f_{CON}<I_T^T>$$

or, respectively, when utilizing the sequence information of the inversely complementary strand, $$f_{MET}=1-I_A^{CG}/f_{CON}<I_A^A>$$

wherein $I_T^{CG}$ represents the thymine signal intensity of a cytosine in CpG position and $<I_T^T>$ the average thymine signal intensity at thymine positions;

and wherein $I_A^{CG}$, respectively, represents the adenine signal intensity of a guanine in CpG position and $<I_A^A>$ the average adenine signal intensity at adenine positions; and wherein a methylation number of 1 corresponds to a 100% methylation.

Further, according to the invention, a method is particularly preferred in which the alignment of a sequence of bases of only one base type, at a nucleotide sequence containing at least three different nucleotides that are only partially known is produced by means of the probabilistic method after determining the distances between two random, individual bases by means of statistical and signal theoretical methods.

Two method variants, which are configured as follows according to the invention, fall under the general inventive concepts.

First, a method for determining the degree of methylation of a cytosine to be investigated in the genome of at least one cell or at least one organism, in which the following steps are conducted:

a) Treatment of a DNA sample with bisulfite and subsequent amplification of a selected fragment of this treated DNA;
b) Conducting a sequence analysis of the amplificate, in which the different bases of the DNA are analyzed either in spatially separate lanes or are analyzed, by different color labels in a distinguishable manner within one lane, and in which the result is represented in the form of an electropherogram;
c) Standardizing of the average signal intensity of at least one base type (C, T, A or G) against the average signal intensity which is obtained for one or more of the remaining base types, wherein the average of a plurality of positions of this base type is determined within an arbitrarily defined region of the amplificate.
d) Determination of a conversion rate of cytosine to uracil as a consequence of bisulfite treatment, hereby characterized in that a ratio of at least one signal intensity standardized in step c) at positions which modify their hybridization behavior due to bisulfite treatment to at least one other signal intensity is determined, wherein, both the sense sequence or its inversely-complementary sequence can be utilized;
e) Calculation of the actual degree of methylation of the cytosine to be investigated taking into consideration the standardized signal intensities and the conversion rate determined in step d).

And secondly, a method for determining the degree of methylation of a cytosine to be investigated in the genome of at least one cell or one organism, in which the following steps are conducted:

a) Treatment of a DNA sample with bisulfite and subsequent amplification of a selected fragment of this treated DNA;
b) Conducting a sequence analysis of the amplificate, in which only the thymine, or in the inversely-complementary strand only the adenine, sequence of the DNA is determined and the result is represented in the form of an electropherogram;
c) Determination of a conversion rate of cytosine to uracil as a consequence of bisulfite treatment, hereby characterized in that the ratio of the signal intensity of bases which modify their hybridization behavior due to bisulfite treatment to the signal intensity of bases which do not modify their hybridization behavior due to bisulfite treatment is determined, wherein, both the sense sequence or its inversely-complementary sequence can be utilized;
d) Calculation of the actual degree of methylation of the cytosine to be investigated taking into consideration the conversion rate determined in step c).

BRIEF DESCRIPTION OF THE DRAWINGS

FIG. 2: Two complex electropherograms are shown. The numbers at the lower edge of the figure describe the base positions within the sequenced amplificate and serve for orientation. In FIG. 2, both electropherograms extend from base 322 to base 379 (SEQ ID NO: 4). The upper electropherogram describes the sequence of the four different bases (in four different colors: T=red, C=blue, A=green, G=black) without standardization or consideration of the conversion rate, thus without applying the present invention. The electropherogram below describes the data, as they appear after application of one variant of the invention described herein. The percentages given below the cytosines in CpG position give the degree of methylation of the cytosine after calculation based on the method described herein.

DETAILED DESCRIPTION OF THE INVENTION

The invention is described in more detail below. The invention describes a method for the quantitative sequencing of nucleic acids treated with bisulfite, or more precisely stated, a method for determining the degree of methylation of one or more cytosines in the base sequence 5'-CG-3', thus in a so-called CpG position, if the genomic sequence of the investigated DNA region is known. The invention particularly describes a method for determining the fraction of nucleic acid molecules, which are methylated in the CpG position, from a mixture of nucleic acids, which have methylated and unmethylated cytosines, based on a sequence analysis of the mixture of nucleic acids treated with bisulfite. The invention enables the validation of sequence information in the sequencing of DNA treated with bisulfite. It is particularly described how the data obtained with conventional sequencing methods are first standardized with respect to their signal intensity, how the conversion rate of cytosine to uracil as a consequence of bisulfite treatment is determined from these data, and how an essentially improved estimation of the degree of methylation actually present is obtained with the help of this conversion rate.

In the present invention, it is shown in detail both how the signal intensities of electropherograms are standardized relative to one another and also how the conversion rate of the bisulfite reaction is calculated on the basis of the information obtained in the electropherogram. It is described how basically more accurate information on the fraction of methylated cytosines in a mixture of methylated and unmethylated cytosines can be obtained by means of these factors. Therefore, the invention has proven extremely useful for the analysis of degrees of methylation of DNA samples and thus also improves, for example, the diagnosis of methylation-specific diseases.

The invention extends to the analysis of DNA mixtures both in individual cells as well as of DNA mixtures from a plurality of cells, which can originate either from one organism or from different organisms. The method for the determination of the degree of methylation of at least one cytosine to be investigated in the genome of at least one such cell, which is described in this Application, presumes that the genomic nucleotide sequence of the DNA not treated with bisulfite is known. In the first step of the method, the genomic DNA sample to be investigated is treated with bisulfite, whereby unmethylated cytosine bases are modified such that they have a hybridization behavior like thymine bases in the subsequent PCR, while the 5-methylcytosine bases remain unchanged. The double-stranded DNA amplificates obtained by PCR contain a thymine instead of an unmethylated cytosine in the sense strand and correspondingly, an adenine on the inversely complementary strand. Consequently, by determining the thymine signal intensities at original cytosine positions in CpG position, the fraction of unmethylated cytosines can be determined at this CpG position in the present mixture.

The subject of the invention is a first method variant according to the invention, in which the amplificates are first sequenced and the labeled reaction products are then subsequently analyzed according to their size either in spatially separated lanes or by different color labels distinguishable within one lane. For example, four different fluorescently-labeled ddNTPs can be used, but it is also possible to limit the analysis to the determination of fewer than four base sequences. In the prior art, the sequence analysis concludes with an electropherogram which can only be used for a qualitative determination of the base sequence. The present invention describes how quantitative information with respect to the degree of methylation of a cytosine can also be obtained from this electropherogram and from the comparison of these data with the original sequence, that is the sequence of the DNA not treated with bisulfite.

First, a standardization of the electropherogram data is produced for this purpose. The ratio of the average signal intensity of at least one base type (C, T, A or G) to the average signal intensity of one or more of the other base types is determined. In a particularly preferred variant of the method, the ratio of the signal intensity of cytosine to that of thymine is determined. The average is calculated each time via the signal intensities of bases, which are present in a randomly defined region of the amplificate. This can comprise the entire amplificate or only one small segment of it.

In the next step a conversion rate of cytosine to uracil as a consequence of bisulfite treatment ($f_{CON}$) is calculated from the standardized signal intensities. This describes the ratio of unmethylated cytosine bases, whose hybridization behavior was modified by bisulfite treatment into the hybridization behavior of thymine, to all unmethylated cytosine bases, independent of whether their hybridization behavior was modified or not, within a defined sequence region. The region to be considered can comprise the length of the total amplificate or only a part of it.

Taking into consideration the standardizing and with the help of this conversion rate $f_{CON}$, in the last step, the actual methylation number $f_{MET}$, or at least a methylation number close to reality, is determined.

The subject of the invention is a second, related method variant for the determination of this methylation number, for the case when, in addition to the known genomic nucleotide sequence of the DNA not treated with bisulfite, whose knowledge is a prerequisite for determining the degree of methylation, only the thymine electropherogram of the DNA treated with bisulfite will be or can be used for the analysis. The subject of the invention is first how a conversion rate $f_{CON}$ can be determined from the thymine electropherogram alone, without knowledge of the cytosine, guanine and adenine base sequences, and how the methylation number can be calculated with its help. For this case, the calculation of the conversion rate is of even greater importance, since a standardizing of the data is neither possible nor necessary.

Preferred are variants of both methods characterized in that the cytosine signal intensities are standardized relative to the thymine signal intensities.

The calculation of the standardizing factors, for standardizing of signal intensities, as well as the calculation of the conversion rate are based on knowledge of signal intensities that is as accurate as possible.

In a preferred variant of the first method, standardizing factors are calculated as follows:

Since the electropherogram represents a curve which reflects the number of detected signals per unit of time, which in turn reflects the spatial distance between two bases (as an inherent characteristic of the sequencing method), the signal intensity and thus the number of molecules which bear that signal can be calculated by the area under the peak, thus under the local maximum of this curve. The considered area can be best described by integrating this curve. These area measurements are determined by the integration limits X1 and X2. The integrals are formed each time by a value X1, lying to the left of the local maximum, up to a value X2, lying to the right of the local maximum. For the calculation of the signal intensity, the following possible limiting values are particularly preferred herein for integrating the areas under the local maxima.

Thus the method is particularly preferred when the numerical quantities for the signal intensity are produced either by
- Integrating the area under the signal curve from the point of inflection on the left lying closest to the local maximum to the point of inflection lying closest to it on the right,
- Integrating the area under the signal curve from the local minimum lying closest to the local maximum on the left to the local minimum lying closest to it on the right,
- Integrating the area under the signal curve from the half-height point lying closest to the local maximum on the left, thus the x-coordinate of the value which amounts to the half-height ($\frac{1}{2} f(x)$) of the local maximum, to the half-height point lying closest to the local maximum on the right, Integrating the area under the signal curve from a value D1 to a value D2, whereby D1 and D2 describe the x-coordinates, which lie precisely in the center each time, between two local maxima, whereby D1 is found to the left of the maximum to be determined and D2 is found to the right of the maximum to be determined, Or by integrating the area under the signal curve by involving any combination of the described limiting values.

A variant of both methods is preferred, which is characterized in that the bisulfite sequence information used was determined by means of the chain termination method.

A method is particularly preferred, in which the standardizing factor can be calculated from the ratio of the average cytosine signal intensity at cytosines in CpG position, to the difference between the average thymine signal intensity at thymines and the average thymine signal intensity at cytosines in CpG position:

$$f_N = <I_C^{CG}>/(<I_T^T> - <I_T^{CG}>)$$

or from its reciprocal value $$f_{N-1} = (<I_T^T> - <I_T^{CG}>)/<I_C^{CG}>$$

It is obvious and thus included in the preferred variants that thymine and cytosine signal intensities can be replaced herein by adenine and guanine signal intensities, if the sequence data of the inversely complementary strand are used for conducting the method:

$$f_N = <I_G^{CG}>/(<I_A^A> - <I_A^{CG}>)$$

or from its reciprocal value $$f_{N-1} = (<I_A^A> - <I_A^{CG}>)/<I_G^{CG}>$$

A variant of the first method is most particularly preferred, which is characterized in that the standardizing factor can be calculated from the ratio of the average cytosine signal intensity at cytosines other than those in CpG positions, to the difference between the average thymine signal intensity at thymines and the average thymine signal intensity at cytosines other than those in CpG positions:

$$f_N = <I_C^C>/(<I_T^T> - <I_T^C>)$$

or from its reciprocal value $$f_N^{-1} = (<I_T^T> - <I_T^C>)/<I_C^C>$$

It is also obvious here, and thus included in the preferred variants, that thymine and cytosine signal intensities can be replaced herein by adenine and guanine signal intensities, if the sequence data of the inversely complementary strand are utilized for conducting the method:

$$f_N = <I_G^G>/(<I_A^A> - <I_A^G>)$$

or from its reciprocal value $$f_{N-1} = (<I_A^A> - <I_A^G>)/<I_G^G>$$

A variant of the method is also particularly preferred, which is characterized in that the standardizing factor can be calculated from the ratio of the average thymine signal intensity at adenine and guanine positions to the average cytosine signal intensity at guanine positions:

$$f_N = <I_T^{A,G}>/<I_C^{A,G}>$$

or from its reciprocal value $$f_{N-1} = <I_C^{A,G}>/<I_T^{A,G}>$$

And vice versa, when utilizing the bisulfite sequence data of the inversely complementary strand the calculation of this standardizing factor can preferably be calculated from the ratio of the average adenine to guanine signal intensities at thymine and cytosine positions:

$$f_N = <I_A^{T,C}>/<I_G^{T,C}>$$

or from its reciprocal value $$f_{N-1} = <I_G^{T,C}>/<I_A^{T,C}>$$

For all named calculations of the average values, it applies that these are always averaged over an established sequence region which can comprise both either the length of the total amplificate or only a minimum number of bases.

In a further step, the method contains the determination of a conversion rate $f_{CON}$.

A variant of the first method is particularly preferred which is characterized in that a conversion rate $f_{CON}$ is calculated from the ratio of cytosines converted to thymine to the sum of all cytosines, which are converted and unconverted, within a defined sequence region. For this purpose, the ratio of thymine signal intensities at positions, which were occupied by cytosine before the bisulfite treatment and are not CpG positions to the sum of these thymine and standardized cytosine signal intensities at said positions is calculated:

$$f_{CON} = I_T^C/(f_N I_C^C + I_T^C)$$

or $$f_{CON} = <I_T^C/(f_N I_C^C + I_T^C)>$$

or from its reciprocal value $$f_{CON-1} = (f_N I_C^C + I_T^C/I_T^C)$$

or $$f_{CON}^{-1} = <(f_N I_C^C + I_T^C)/I_T^C>$$

or, respectively, when utilizing the sequence information of the inversely complementary strand:

$$f_{CON} = I_A^G/(f_{NG}^G + I_A^G)$$

or $$f_{CON} = <I_A^G/(f_N I_G^G + I_A^G)>$$

or from its reciprocal value $$f_{CON}^{-1} = (f_N I_G^G + I_A^G)/I_A^G$$

or $$f_{CON}^{-1} = <(f_N I_G^G + I_A^G)/I_A^G>$$

In addition, a variant of both methods is preferred, which is characterized in that this conversion rate can also be calculated by means of the thymine signal intensities only. For this purpose, the ratio of the thymine signal intensity at a position which was occupied by cytosine prior to bisulfite treatment, but is not found in a CpG position, to the thymine signal intensity at a thymine position is formed.

$$f_{CON} = <I_T^C>/<I_T^T>$$

or from its reciprocal value $$f_{CON}^{-1} = <I_T^T>/<I_T^C>$$

or, respectively, when utilizing the sequence information of the inversely complementary strand, $$f_{CON} = <I_A^G>/<I_A^A>$$

or from its reciprocal value $$f_{CON}^{-1} = <I_A^A>/<I_A^G>$$

In all described preferred variants of the method for calculating the conversion rate, either the average values over several such positions in a defined sequence region are utilized or individual values are utilized, in order to determine either the conversion rate for a sequence region or the conversion rate of a single cytosine.

A variant of the first method is also preferred which is characterized in that, with the help of the standardizing factor and the conversion rate determined for each cytosine, which is found in a CpG position within the investigated sequence region, a methylation number $f_{MET}$ is calculated, which takes into consideration both the occasionally limited efficiency of the bisulfite reaction as well as the partially very greatly falsified signal intensities. This is done by applying the following formula:

$$f_{MET}=1-I_T^{CG}/(f_{CON}(f_N I_C^{CG}+I_T^{CG})).$$

Herein, all signal intensities I refer to the cytosine in CpG position: $I^{CG}$. $I_T^{CG}$ describes the signal intensity of the thymine at this cytosine, thus the fraction of the unconverted cytosines. This value approximates the actual value due to involving the conversion rate $f_{CON}$. $I_C^{CG}$ describes the cytosine signal intensity at this cytosine in CpG position. $I_C^{CG}$ describes both the methylated cytosines as well as the unmethylated cytosines, but not converted cytosines in CpG position and approximates the actual value by involving a standardizing factor $f_N$. Lastly, $f_{MET}$ accurately describes the percentage of actually methylated cytosines, whereby $f_{MET}$ can take values between 0 and 1.

If the cytosine in the CpG position is completely methylated (methylation 100%), this corresponds to an $f_{MET}$ of 1. This is the case if a thymine signal is not obtained (thus $I_T^{CG}=0$). Then the following applies:

$$f_{MET}=1-0/(f_{CON}(f_N I_C^{CG}+0))=1$$

If the cytosine in the CpG position is not methylated (methylation 0%), this corresponds to an $f_{MET}$ of 0. If a 100% conversion results, thus a conversion rate $f_{CON}=1$, a cytosine signal is not obtained and the following applies:

$$f_N I_C^{CG}=0.$$

Thus we have:

$$f_{MET}=1 I_T^{CG}/(f_{CON} I_T^{CG})=1-1/f_{CON}=0$$

However, if a 100% conversion has not occurred, cytosine signals are also always obtained, even if the cytosines are not methylated.

In the case of only up to 50% methylated cytosine positions and up to 100% conversion produced, the fractions of standardized cytosine signal and thymine signal are of the same magnitude. The following applies:

$$f_{MET}=1-I_T^{CG}/(f_{CON}(f_N I_C^{CG}+I_T^{CG})$$

$$f_{MET}=1-I_T^{CG}/(f_{CON}(2*I_T^{CG}))$$

$$f_{MET}=1-1/(f_{CON}*2)$$

$$f_{MET}=1-\tfrac{1}{2}$$

It is always true that when utilizing sequence information of the inversely complementary strand, the same formulas apply, but all thymines must be replaced by adenines and all cytosines by guanines, thus for example:

$$f_{MET}=1-I_A^{CG}/(f_{CON}(f_N I_G^{CG}+I_A^{CG}))$$

A variant of the second method is also preferred which is characterized in that when using as a basis a sequence of only one base, i.e., the thymine sequence, of the DNA treated with bisulfite, a methylation number $f_{MET}$ is calculated according to the following formula:

$$f_{MET}=1-I_T^{CG}/f_{CON}<I_T^T>$$

For this purpose, the average thymine signal intensity at thymines $<I_T^T>$ is applied. Or, respectively, when utilizing the sequence information of the inversely complementary strand, the following formula applies:

$$f_{MET}=1-I_A^{CG}/f_{CON}<I_A^A>$$

wherein the average adenine signal intensity at adenines $<I_A^A>$ is applied.

In both cases, it is true that $f_{MET}$ can take values between 0 and 1 and a methylation number of 1 corresponds to a 100% methylation.

In the variant of the method which is applied in the presence of a sequence of only one base, i.e., the thymine sequence or, respectively, when utilizing the inversely complementary strand, the adenine sequence, the difficulty arises of not being able to clearly assign the signal intensities. A sequence, which has no thymines and gives, as the case may be, only minimal signals, so-called error signals, over a relatively long region, can only with difficulty be assigned to its known genomic nucleotide sequence. This is even more difficult if considering that the present one-base sequence must be assigned to a nucleotide sequence treated with bisulfite, which is known only to a limited extent.

Thus, a variant of the method which concerns this other subject of the invention is particularly preferred, in which the distance between two peaks, thus between two potential base positions is first determined with statistical and theoretical signal methods and then the assignment to known positions derived from the genomic sequence is carried out by means of the probabilistic method.

The following examples explain the invention.

EXAMPLE 1

Investigation of the degree of methylation of the p16 gene by means of sequence analysis.

The following example refers to a fragment of the p16 gene, in which specific CpG positions are investigated with respect to their degree of methylation. In this example, the DNA was commercially obtained and had been previously isolated from human blood by the supplier.

In the first step, a genomic sequence is treated with the use of bisulfite (hydrogen sulfite, disulfite) in such a way that all of the cytosines unmethylated at the 5-position of the base are modified such that a base that is different in its base-pairing behavior is formed, while the cytosines that are methylated in the 5-position remain unchanged. If bisulfite is used for the reaction, then an addition occurs on the unmethylated cytosine bases. Also, a denaturing reagent or solvent as well as a radical trap must be present. A subsequent alkaline hydrolysis then leads to the conversion of unmethylated cytosines to uracil. This converted DNA serves for the purpose of distinguishing methylated cytosines from unmethylated cytosines and thus detecting these. In the second step of the method, the treated DNA sample is diluted with water or an aqueous solution. Preferably, a DNA desulfonation is then conducted. In another step [of the method], the DNA sample is amplified in a polymerase chain reaction, preferably with a heat-stable DNA polymerase. In the present case, cytosines of the p16 gene are investigated. For this purpose, a defined fragment of 256 bp in length is amplified with the specific primer oligonucleotides P1 (see Seq-ID 1) and P2 (see Seq-ID 2). The present PCR product is a DNA mixture of amplificates, which have either cytosines or thymines at the CpG positions to be investigated. This mixture of amplificates serves as a template for a subsequent cyclic sequencing reaction. The same primer oligonucleotides are used for the sequencing reaction as are used for the polymerase chain reaction. The result of sequencing is represented in FIG. 1 in the form of electropherograms.

Figure 1:
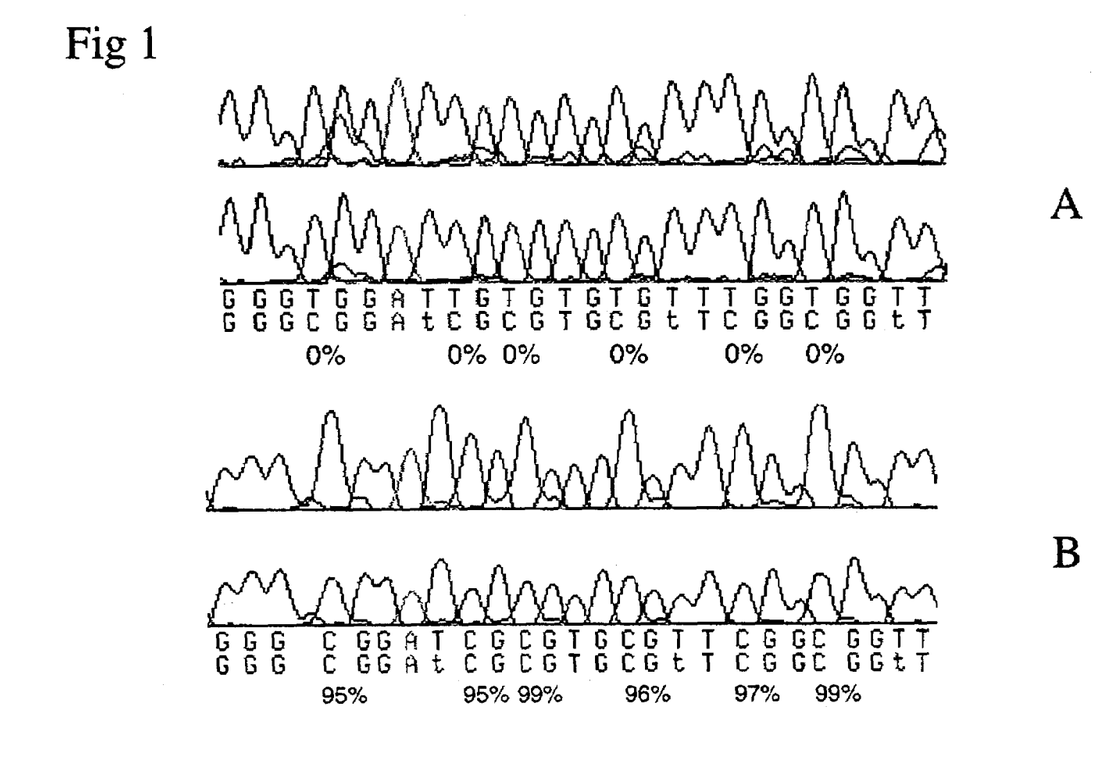
FIG. 1: Two electropherograms are shown in the upper part of FIG. 1 (electropherogram pair A) which show a partial region of the sequence of the p16 gene (SEQ ID NO: 1: unmethylated, converted and SEQ ID NO: 2: methylated, converted), in the methylation state which was indicated in the commercial acquisition of the DNA mixture. In the lower part of the figure (electropherogram pair B), two electropherograms are shown, which represent the same sequence region (SEQ ID NO: 3), wherein the DNA was methylated in a previous step. According to this, the degrees of methylation of the cytosines reach almost 100%.

Two electropherograms are shown in the upper part of FIG. 1 (electropherogram pair A) and these portray a partial region of the sequence of the p16 gene, in the methylation state which was indicated in the commercial acquisition of the DNA mixture. In the lower part of the figure (electropherogram pair B), two electropherograms are shown, which represent the same sequence region. The difference in comparison to the upper part of the figure is that the DNA, which serves as the basis for this sequencing, was methylated in a previous step. According to this, the degrees of methylation of the cytosines reach almost 100%.

Each of the upper electropherograms of the electropherogram pairs A and B describe the sequences, as they are generated by the software of the automatic sequencer. Therefore, they show a commercially obtained electropherogram. Each of the lower electropherograms of the electropherogram pairs A and B describe the sequences, as they are shown after applying the invention described herein. The appearance of extraneous signals, thus the background noise, is clearly reduced.

Two sequences are shown underneath the electropherograms as sequences of letters, which indicate the respective bases. Each top base sequence is referred to the lower, optimized electropherogram, while, in contrast, each bottom base sequence shows the theoretically expected sequence, as it is expected in the known genomic sequence after bisulfite treatment, and serves for comparison to the data generated by the automatic sequencer.

A stands for adenine, C stands for cytosine, G stands for guanine, T stands for thymine, and t is indicated at base positions which only display the hybridization behavior of thymine after bisulfite treatment, but were previously cytosines in the genomic sequence. (In the color representation, the bases are represented in four different colors: thymine=T=red, cytosine=C=blue, adenine=A=green, guanine=G=black.)

Numbers are indicated underneath the base sequence. They give the respective percent degree of methylation of a cytosine in CpG position, as calculated by applying the method described herein.

EXAMPLE 2

Figure 2:
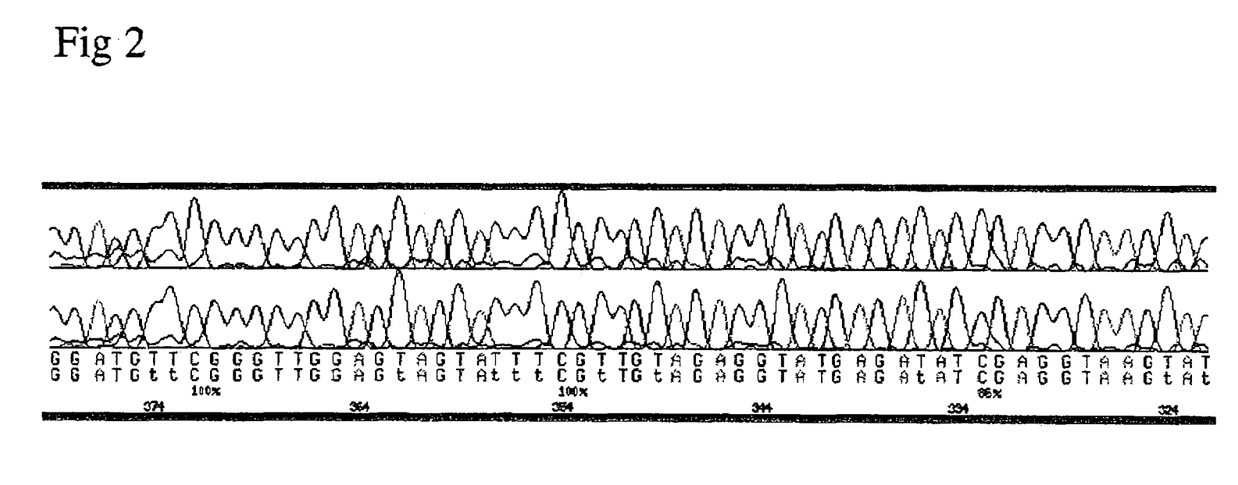

Representation of electropherograms after bisulfite sequencing with and without use of the method according to the invention:

Two complex electropherograms are portrayed one over the other in FIG. 2. The numbers at the lower edge of the figure describe the base positions within the sequenced amplificate and serve for orientation. In FIG. 2, both electropherograms extend from base 322 to base 379. The upper electropherogram describes the sequence of the four different bases (in four different colors: thymine=T=red, cytosine=C=blue, adenine=A=green, guanine=G=black) without standardization or consideration of the conversion rate, thus without applying the present invention. The electropherogram below describes the data, as they appear after application of one variant of the invention described herein. It can be clearly recognized that the cytosine signals in the upper electropherogram are all essentially greater than in the lower electropherogram, after the cytosine signal intensity was standardized. Likewise, the "noise" is also smaller, which can be recognized quite well, for example, in the region from bp 373 to 379. The percentages given below the cytosines in CpG position give the degree of methylation of the cytosine after calculation based on the method described here.

The invention claimed is:

1. A method for determining the degree of methylation of a cytosine to be investigated in the genome of at least one cell or one organism, characterized in that the following steps are conducted:
   a) treating a DNA sample with bisulfite and subsequently amplifying a selected fragment of this treated DNA to produce an amplificate;
   b) conducting a sequence analysis of at least two different bases of the amplificate, in which the result is represented in the form of a DNA sequencing electropherogram, wherein the sequence of bases is represented as a curve plot, said conducting step comprising calculating the signal intensity of each base by the area under the peak, standardizing the average signal intensity of at least one, but not all, base types (C, T, A, G) against the average signal intensity obtained for one or more of the remaining base types, and determining the average of at least two positions of this base type within an arbitrarily defined region of the amplificate;
   c) determining a conversion rate at which unmethylated cytosine bases are converted to uracil bases as a consequence of bisulfite treatment, wherein less than all of said unmethylated cytosine bases are converted to uracil following bisulfite treatment, wherein said determining comprises quantitatively comparing the signal intensity of bases which, prior to bisulfite treatment, were unmethylated cytosine bases and which, following bisulfite treatment, exhibited a change in hybridization behavior from that of a cytosine base relative to the signal intensity of bases which, prior to bisulfite treatment, were unmethylated cytosine bases and which, following bisulfite treatment, did not exhibit a change in hybridization behavior from that of a cytosine base, wherein the sense sequence and/or its complementary sequence is used for said determination of the conversion rate;
   d) calculating the actual degree of methylation of the cytosine to be investigated taking into consideration the conversion rate determined in step c).

2. The method according to claim 1, further characterized in that, in the sequence analysis of the amplificate, only the sequence of thymine bases, or in the complementary strand only the sequence of adenine bases, of the DNA is determined and the result is presented in the form of an electropherogram.

3. The method according to claim 2, wherein an alignment of a sequence of bases of only one base type to positions derived from the genomic nucleotide sequence is produced by means of probabilistic methods after determining the distances between two arbitrary, individual bases with the help of statistical and signal theoretical methods.

4. The method according to claim 1 or 2, in which the signal intensity $I_B$ of a base B, wherein B can be either C, A, G or T, and thus establishes the type of base whose intensity is determined, is described as a part of the area under the peak in the electropherogram by the following formula, wherein f(x) describes the curve of the intensity signal over a unit x, which represents the time, which describes the distance between two bases after chromatographic separation $$I_B = \int_{W1}^{W2} f(x)\,dx$$

wherein W1 and W2 are the x-coordinates of the points of inflection lying closest to the x value of the maximum $f_{max}$ and W1 lies to the left and W2 to the right of this x value.

5. The method according to claim 1 or 2, in which the signal intensity $I_B$ is described by the following formula:

$$I_B = \int_{M1}^{M2} f(x)\,dx$$

wherein M1 and M2 are the x-coordinates of the minima lying closest to the x value of the maximum $f_{max}$ and M1 lies to the left and M2 to the right of this x value.

6. The method according to claim 1 or 2, in which the signal intensity $I_B$ is described by the following formula:

$$I_B = \int_{H1}^{H2} f(x)\,dx$$

wherein H1 and H2 are the x-coordinates of the positions in the curve at which f(x) is one-half $f_{max}$, lying closest to the x value of the maximum $f_{max}$, and H1 lies to the left and H2 to the right of this x value.

7. The method according to claim 1 or 2, in which the signal intensity $I_B$ is described by the following formula:

$$I_B = \int_{D1}^{D2} f(x)\,dx$$

wherein $D1 = x - (x - x\_\text{left})/2$ and $D2 = x + (x\_\text{right} - x)/2$, wherein
   x is the x-coordinate of the position A of the signal intensity to be determined
   x_left is the x-coordinate of the maximum of the peak to the left thereof and
   x_right is the x-coordinate of the maximum of the peak to the right thereof.

8. The method according to claim 1 or 2, in which the signal intensity $I_B$ of a signal at a position A can be calculated as the area under the signal curve according to the following formula:

$$I_B = \int_{X1}^{X2} f(x)\,dx$$

wherein the x-coordinates of a random combination of W1, W2, H1, H2, M1, M2, D1 or D2 can be used as limiting values X1 and X2, wherein W1 and W2 are the x-coordinates of the points of inflection lying closest to the x value of the maximum $f_{max}$ and W1 lies to the left and W2 to the right of this x value, wherein H1 and H2 are the x-coordinates of the positions in the curve at which f(x) is one-half $f_{max}$, lying closest to the x value of the maximum $f_{max}$, and H1 lies to the left and H2 to the right of this x value, wherein M1 and M2 are the x-coordinates of the minima lying closest to the x value of the maximum $f_{max}$ and M1 lies to the left and M2 to the right of this x value, and wherein D1=x−(x−x_left)/2 and D2=x+(x_right−x)/2 wherein x is the x-coordinate of the position A of the signal intensity to be determined, x_left is the x-coordinate of the maximum of the peak to the left thereof and x_right is the x-coordinate of the maximum of the peak to the right thereof, but X1 must lie to the left and X2 to the right of the x-value that determines position A.

9. The method according to claim 1 or 2, in which the sequence analysis is conducted according to a chain termination method.

10. The method according to claim 1, further characterized in that the standardized average signal intensities in step b) are used for the determination of the named conversion rates in step c).

11. The method according to claim 1, further characterized in that both the standardized average signal intensities and the conversion rates which are obtained taking into consideration the standardized average signal intensities are used for the calculation of the actual degree of methylation of the cytosine to be investigated.

12. The method according to claim 1, further characterized in that the signal intensity of the cytosine signals is standardized against the signal intensity of the thymine signals or, when utilizing the sequence information of the complementary strand, the signal intensity of the guanine signals is standardized against the signal intensity of the adenine signals.

13. The method according to claim 1, wherein the factor for standardizing $f_N$ is calculated from $$f_N = <I_C^{CG}>/(<I_T^T> - <I_T^{CG}>)$$

or from its reciprocal value $$f_N^{-1} = (<I_T^T> - <I_T^{CG}>)/<I_C^{CG}>$$

or, respectively, when utilizing the sequence information of the complementary strand, $$f_N = <I_G^{CG}>/(<I_A^A> - <I_A^{CG}>)$$

or from its reciprocal value $$f_N^{-1} = (<I_A^A> - <I_A^{CG}>)/<I_G^{CG}>$$

wherein $<I_T^T>$ represents the average thymine signal intensity ($I_T$) at positions that were thymine prior to bisulfite treatment and $<I_A^A>$ represents the average adenine signal intensity ($I_A$) at positions that were adenine prior to bisulfite treatment;
wherein $<I_T^{CG}>$ and $<I_C^{CG}>$ are the average thymine and cytosine signal intensities at cytosines in CpG positions; and wherein $<I_A^{CG}>$ and $<I_G^{CG}>$, respectively, represent the average adenine and guanine signal intensities at guanines in CpG positions; and wherein the average of all of the considered positions is taken each time within a randomly defined sequence region.

14. The method according to claim 1, wherein the factor for standardizing $f_N$ is calculated from $$f_N = <I_C^C>/(<I_T^T> - <I_T^C>)$$

or from its reciprocal value $$f_N^{-1} = (<I_T^T> - <I_T^C>)/<I_C^C>$$

or, respectively, when utilizing the sequence information of the complementary strand, $$f_N = <I_G^G>/(<I_A^A> - <I_A^G>)/<I_G^G>$$

or from its reciprocal value $$f_N^{-1} = (<I_A^A> - <I_A^G>)/<I_G^G>$$

wherein $<I_T^T>$ represents the average thymine signal intensity ($I_T$) at positions that were thymine prior to bisulfite treatment and $<I_A^A>$ represents the average adenine signal intensity ($I_A$) at positions that were adenine prior to bisulfite treatment;
wherein $<I_T^C>$ and $<I_C^C>$ represent the average thymine and cytosine signal intensities, respectively, at cytosines and $<I_A^G>$ and $<I_G^G>$ represent the average adenine and guanine signal intensities, respectively, at guanines, which are not located in CpG positions,
and wherein the average of all of the considered positions is taken each time within a randomly defined sequence region.

15. The method according to claim 1, wherein the factor for standardizing $f_N$ is calculated from $$f_N = <I_T^{A,G}>/<I_C^{A,G}>$$

or from its reciprocal value $$f_N^{-1} = <I_C^{A,G}>/<I_T^{A,G}>$$

or, respectively, when drawing on the sequence information of the complementary strand, $$f_N = <I_A^{T,C}>/<I_G^{T,C}>$$

or from its reciprocal value $$f_N^{-1} = <I_G^{T,C}>/<I_A^{T,C}>$$

wherein $>I_T^{A,G}>$ represents the average thymine signal intensity ($I_T$) at adenine or guanine positions and $<I_C^{A,G}>$ the average cytosine signal intensity ($I_C$) at adenine or guanine positions;
and wherein $<I_A^{T,C}>$ represents the average adenine signal intensity ($I_A$), and $<I_G^{T,C}>$ represents the average guanine signal intensity ($I_G$) at thymine or cytosine positions; and wherein the average of all of the considered positions is taken each time within a randomly defined sequence region.

16. The method according to claim 1, wherein the conversion rate $f_{CON}$ is calculated from $$f_{CON} = I_T^C/(f_N I_C^C + I_T^C)>$$

or $$f_{CON} = <I_T^C/(f_N I_C^C + I_T^C)>$$

or from its reciprocal value $$f_{CON}^{-1} = (f_N I_C^C + I_T^C)/I_T^C$$

or $$f_{CON}^{-1} = <(f_N I_C^C + I_T^C)/I_T^C>$$

or, respectively, when drawing on the sequence information of the complementary strand, $$f_{CON}=I_A^G/(f_N I_G^G+I_A^G)$$

or $$f_{CON}=<I_A^G/(f_N I_G^G+I_A^G)>$$

or from its reciprocal value $$f_{CON}^{-1}=(f_N I_G^G+I_A^G)/I_A^G$$

or $$f_{CON}^{-1}=<(f_N I_G^G+I_A^G)/I_A^G>$$

wherein, each time depending on which standardization is applied, $f_N$ is the standardization factor according to claim 13, 14 or 15;

wherein $I_T^C$ represents the thymine signal intensity and $I_C^C$ represents the cytosine signal intensity of a cytosine not found in a CpG position, and respectively, $I_A^G$ represents the adenine signal intensity and $I_G^G$ represents the guanine signal intensity of a guanine not found in a CpG position, after bisulfite treatment;

and wherein either the average of the corresponding quotients of all considered positions within a randomly defined sequence region is taken or only one cytosine or guanine position is considered.

17. The method according to claim 1, wherein the conversion rate $f_{CON}$ is calculated from $$f_{CON}^{-1}=<I_T^C>/<I_T^T>$$

or from its reciprocal value $$f_{CON}^{-1}=<I_T^T>/<I_T^C>$$

or, respectively, when drawing on the sequence information of the complementary strand, $$f_{CON}=<I_A^G>/<I_A^A>$$

or from its reciprocal value $$f_{CON}^{-1}=<I_A^A>/<I_A^G>$$

wherein $<I_T^C>$ represents the average thymine signal intensity of a cytosine not found in a CpG position and $<I_A^G>$ represents the average adenine signal intensity of a guanine not found in a CpG position, after bisulfite treatment and $<I_T^T>$ represents the average thymine signal intensity at a thymine position and $<I_A^A>$ represents the average adenine signal intensity at an adenine position, and wherein the average of all of the considered positions is taken within a randomly defined sequence region.

18. The method according to claim 1 in which the methylation number $f_{MET}$ is calculated according to the following formula $$f_{MET}=1-I_T^{CG}/(f_{CON}(f_N I_C^{CG}+I_T CG))$$

or, respectively, when drawing on the sequence information of the complementary strand, $$f_{MET}=1-I_A^{CG}/(f_{CON}(f_N I_G^{CG}+I_A^{CG}))$$

wherein $I_T^{CG}$ and $I_C^{CG}$ represent the thymine and cytosine signal intensities of the investigated cytosine in the CpG position and $I_A^{CG}$ and $I_G^{CG}$, respectively, represent the adenine and guanine signal intensities of the investigated guanine in CpG position; and wherein a methylation number of 1 corresponds to a 100% methylation.

19. The method according to claim 1 in which the methylation number $f_{MET}$ is calculated according to the following formula $$f_{MET}=1-I_T^{CG}/f_{CON}<I_T^T>$$

or, respectively, when drawing on the sequence information of the complementary strand, $$f_{MET}=1-I_A^{CG}/f_{CON}<I_A^A>$$

wherein $I_T^{CG}$ represents the thymine signal intensity of a cytosine in CpG position and $<I_T^T>$ represents the average thymine signal intensity at thymine positions; and wherein $I_A^{CG}$, respectively, represents the adenine signal intensity of a guanine in CpG position and $<I_A^A>$ represents the average adenine signal intensity at adenine positions; and wherein a methylation number of 1 corresponds to a 100% methylation.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Human

<400> SEQUENCE: 1
gggtggattg tgtgtgtttg gtggtt                                    26

<210> SEQ ID NO 2
<211> LENGTH: 26
<212> TYPE: DNA
<213> ORGANISM: Human

<400> SEQUENCE: 2
gggcggatcg cgtgcgttcg gcggtt                                    26

<210> SEQ ID NO 3
<211> LENGTH: 26
<212> TYPE: DNA
<213> ORGANISM: Human

<400> SEQUENCE: 3
gggcggatcg cgtgcgttcg gcggtt                                    26

-continued

```
<210> SEQ ID NO 4
<211> LENGTH: 58
<212> TYPE: DNA
<213> ORGANISM: Human

<400> SEQUENCE: 4
ggatgttcgg gttggagtag tatttcgttg tagaggtatg agatatcgag gtaagtat          58
```